United States Patent [19]

Strickland

[11] 4,215,777
[45] Aug. 5, 1980

[54] SUTURE HOLDING CASE

[76] Inventor: Ola D. Strickland, 3479 Cove Ter., Douglasville, Ga. 30135

[21] Appl. No.: 28,231

[22] Filed: Apr. 9, 1979

[51] Int. Cl.² .................. A61L 17/02; B65D 85/24
[52] U.S. Cl. .................................. 206/63.3; 206/382
[58] Field of Search .................. 206/63.3, 227, 329, 206/380, 382–383, 388, 486, 495, 523, 588–589, 806, 813

[56] References Cited

U.S. PATENT DOCUMENTS

| 4,008,802 | 2/1977 | Freitag | 206/63.3 |
|---|---|---|---|
| 4,034,850 | 7/1977 | Mandel et al. | 206/382 X |
| 4,063,638 | 12/1977 | Marwood | 206/63.3 |
| 4,120,395 | 10/1978 | Mandel et al. | 206/63.3 |
| 4,121,711 | 10/1978 | Bolanowski | 206/63.3 |
| 4,135,623 | 1/1979 | Thyen | 206/63.3 |

FOREIGN PATENT DOCUMENTS 1527094  4/1968  France ................... 206/63.3

Primary Examiner—William T. Dixson, Jr.
Attorney, Agent, or Firm—Newton, Hopkins & Ormsby

[57] ABSTRACT

A flat flexible bag, having opposed walls and open at its upper end for containing strands of various sutures to be employed by a surgeon in an operation. One wall connects to a relatively rigid suture retaining panel which extends above the pocket and is provided with spaced slits through which the sutures respectively pass. Fastening means secures the panel to the edge of an instrument table.

In one embodiment, the sutures pass through a spongy block affixed to the panel.

15 Claims, 5 Drawing Figures

SUTURE HOLDING CASE

BACKGROUND OF THE INVENTION

1. Field of the Invention

This invention relates to a suture holding case and is more particularly concerned with a disposable holder or case which will dispose a normal supply of sutures and needles in a readily available position for a surgical operation.

2. Discussion of the Prior Art

In surgical operations a large number of various types and sizes of sutures must be readily available to the surgeon. Such sutures are usually individually packaged with certain sutures, having no needle and other sutures being prethreaded to the needle. It is the duty of one of the nurses to count these needles, both before and after the operation to assure that all needles are accounted for.

During the operation, the nurse must from time-to-time supply the surgeon with appropriate sutures as the occasion arises. Thus, the burden is upon a nurse to arrange the sutures and their needles in appropriate organization so that a prescribed suture is readily available, when needed.

Numerous racks and holders have been suggested for this purpose. None of these, to my knowledge, have had wide acceptance. Such prior art devices are disclosed in the following U.S. Pat. Nos. 4,105,115; 3,280,971; 1,382,715; 3,338,401; 2,128,701; 3,861,521; 2,692,676; 3,985,227.

Such prior art devices are complex and difficult to use and do not dispose the sutures for ready and immediate access by the nurse.

SUMMARY OF THE INVENTION

Briefly described, the present suture holding case includes a flexible bag formed of a foil, such as paper or fabric, the bag having flat rectangular opposed walls joined along a common transverse bottom edge and common opposed parallel vertically disposed side edges to define an upwardly open common pocket for receiving and carrying the various sutures.

The upper edge portion of one wall is joined to a more rigid suture retaining panel which has rows of spaced staggered holes or slits through which the sutures pass. In one embodiment, a sponge is mounted on the panel and the sutures pass through the sponge and then through the hole or slit.

An adhesive strip on the upper edge of the panel is for adhering the upper edge of the panel to the vertical rim of an instrument table.

It is an object therefore of the invention to provide a suture holding case which is inexpensive to manufacture, durable in structure and efficient in operation.

Another object of the present invention is to provide a suture holding case which will firmly hold preselected strands of sutures, with their needles when specified, in spaced juxtaposition in a common plane for being simultaneously observed and in a position where any one of them may be readily and quickly drawn therefrom for use.

Another object of the present invention is to provide a suture holding case which can be readily and easily installed and removed from an instrument table.

Another object of the present invention is to provide a suture holding case which will hold an array of sutures in a position at the operating field for ready access by a surgeon or nurse during a surgical operation.

Another object of the present invention is to provide a suture holding case which will display the standard or proper sutures for a particular operation with all sutures being in ready view of both the surgeon and the nurse.

Another object of the present invention is to provide a suture holding case and process of supplying sutures in an operating field which will reduce to a minimum the time required for a nurse or surgeon to locate and supply the appropriate sutures which are, from time-to-time, needed in an operation.

Another object of the present invention is to provide a suture holding case which will facilitate the organization and management of sutures and which can be quickly and easily loaded prior to an operation, with the appropriate sutures.

Another object of the present invention is to provide a suture holding case which will keep the sutures properly identified throughout an operation.

Another object of the present invention is to provide a suture holding case which will permit a nurse to withdraw an appropriate suture therefrom at the time that it is requested by the surgeon.

Another object of the present invention is to provide a suture holding case which will organize the sutures prior to operation and display both the sutures and the needles to reduce the time required for counting needles, prior to an operation.

Another object of the present invention is to provide a suture holding case which will enable all persons in the operating arena to know the type and number of sutures available at the operating field so that, should additional sutures be needed, such a need can be anticipated in sufficient time to permit such additional sutures to be brought in.

Another object of the present invention is to provide a suture holding case which will meet the sterility requirements of an operating room.

Another object of the present invention is to provide a suture holding case which is capable of holding a large and diversified array of sutures.

Another object of the present invention is to provide a suture holding case which will reduce the likelihood of the nurse supplying a suture which is knotted, kinked or twisted.

Another object of the present invention is to provide a suture holding case which will reduce the likelihood of a suture or needle being dropped or lost.

Other objects features and advantages will become apparent from the following description when taken in conjunction with the accompanying drawing wherein like characters of reference designate corresponding parts throughout the several views.

DESCRIPTION OF THE PREFERRED EMBODIMENTS

Figure 1:
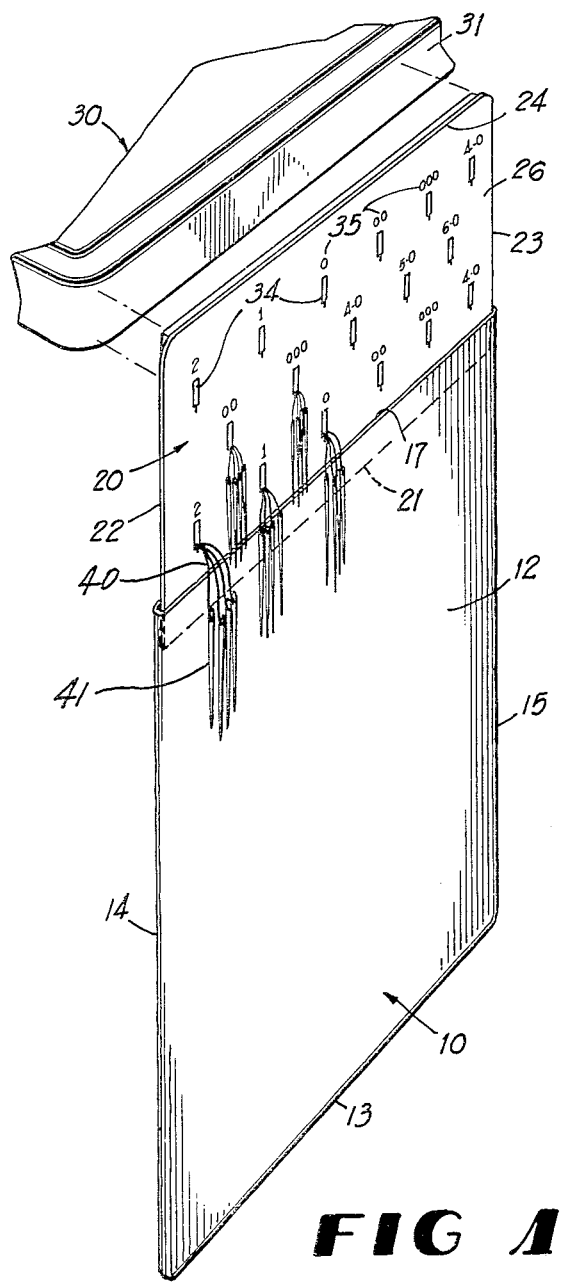
FIG. 1 is an exploded perspective view showing the front and one side of a suture holding case constructed in accordance with the present invention and a portion of an instrument tray to which it is to be attached.

Referring now in detail to the embodiments chosen for the purpose of illustrating the present invention, numeral 10 denotes generally a closure in the form of a flat readily flexible bag, sack or envelope formed of a flexible sheet, web or foil, such as paper, plastic or fabric. Preferably the bag 10 is formed of paper similar to that employed for the disposable operating room slippers and garments.

Bag 10 has a rectangular front wall 11 and an equal size and shape back wall 12. The walls 11 and 12 are joined along a common transverse bottom edge 13 and along common spaced opposed parallel side edges 14 and 15 which are perpendicular to bottom edge 13.

The transverse upper edges 16 and 17 of walls 11 and 12 are disposed parallel to each other and parallel to bottom edge 13. Edge 16 and 17 define an open throat or top opening 18 for the bag 10, so as to provide access to the interior suture pocket defined by wall 11 and 12.

Cooperating with the bag 10 is a rectangular suture retaining panel 20, which is of a width slightly shorter than the width of the bag 10. The panel 20 has a transverse bottom edge 21, depicted in broken lines in FIG. 1, parallel, opposed side edges 22 and 23 and a transverse top edge 24. The edges 21 and 24 are parallel to each other and perpendicular to side edges 22 and 23.

The lower edge portion of panel 20 protrudes a short distance through opening 18 and into the pocket of bag 10. Adhesive secures the overlapped lower portion of front surface 26 of panel 20 and the upper inner edge portion of front wall 12 so that the bag 10 can be wholly supported by the panel 20. The height of panel 20 from edge 21 to edge 24 is of a length about half the length of bag 10 from edge 13 to edge 16 and 17.

Along the inner surface 25 of panel 20, adjacent to the upper edge 24 is a transversely extending, pressure sensitive, adhesive strip 27 which has a removable cover strip 28 thereover. Strip 27 extends substantially from edge 22 to edge 23. The function of strip 27 is to provide a fastening means by which the upper edge portion of panel 20 is removably adhered to rim 31 of an instrument table 30, known as a "Mayo" and will hang pendant on both sides of panel 20.

The panel 20 is preferably made from a sheet of plastic sheet material which is sufficiently rigid to hold open the opening 18.

A plurality of spaced suture receiving openings or holes 34 are provided in the plastic panel 20. Preferably the holes 34 are arranged in equally spaced horizontal rows, the holes 34 being equally spaced from each other in each row.

The holes 34 in one row are staggered with respect to the holes 34 of the next adjacent row. Indicia 35 adjacent to each hole on the front surface 26 identify the type and size of the sutures carried by each hole 34.

In the embodiment shown in FIGS. 1, 2 and 3, the hole 34 is illustrated as a rectangular opening with a vertical slit 36 below and communicating with the hole 34. A plurality of suture strands 40 of the appropriate size and type are stored for use by being threaded through the holes 34 and intermediate portions thereof are successively wedged downwardly into the slit or slot 36. Such slits 36 functionally, yieldably, hold the sutures or suture strands 40 until they are withdrawn into the hole 34 and then out through the hole 34.

Figure 2:
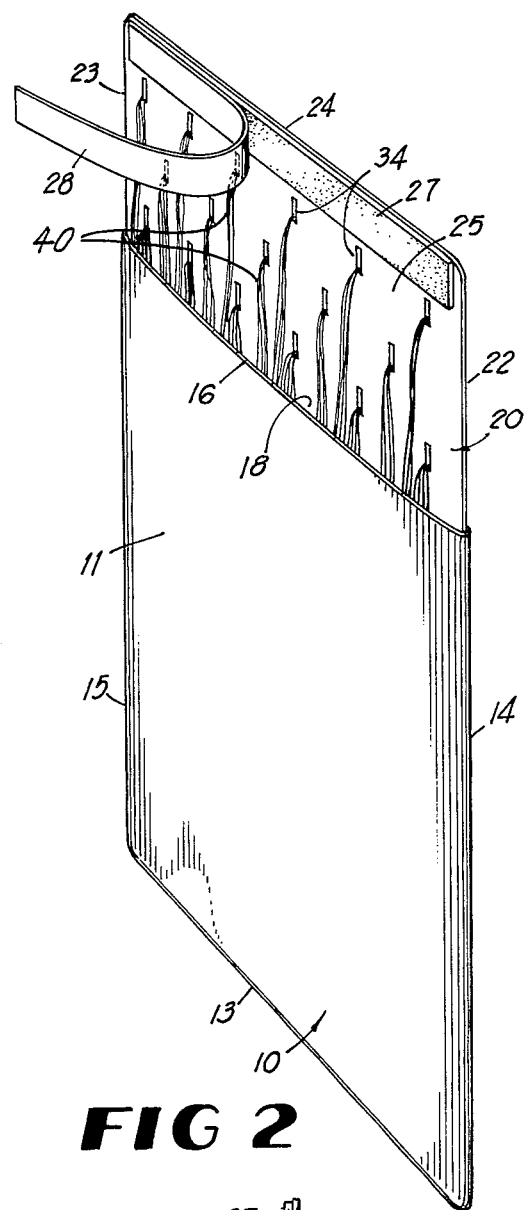
FIG. 2 is a perspective view showing the rear and other side of the suture holding case shown in FIG. 1, the cover strip for the adhesive strip being partially removed.
Figure 3:
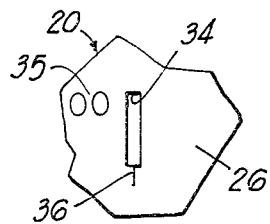
FIG. 3 is an enlarged fragmentary front view of a detail showing one form of suture hole in the panel of the case of FIG. 1.

The bulk of each suture 40 is on the inner side of the panel 20 and hangs downwardly from its hold 34, as shown in FIG. 2, so that is is received and supported in the pocket of bag 10. All the sutures 40 are, thus, in the common pocket of bag 10. The portion or increment of each suture 40 outwardly of the panel 40 hangs downwardly and if such suture contains a needle 41, it is disposed on the outer side of panel 20 on the end portion of its suture 40 as depicted in FIG. 1.

Figure 4:
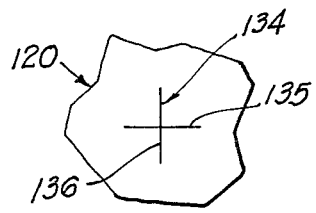
FIG. 4 is a view similar to FIG. 3 and showing a modified form of suture hole in the panel.

If desired in place of the hole 34 and its slit 36, each hold in the panel may be a cross slit, such as cross slit 134 formed in panel 120 intersecting horizontal slit 135 and vertical slit 136 as shown in FIG. 4. Sutures 140 are wedged preferably in the vertical slit 136.

Figure 5:
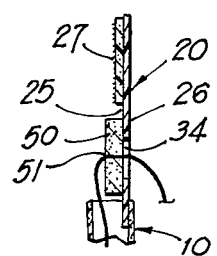
FIG. 5 is a vertical sectional view of a modified form of the present invention.

At times it may be found desirable to provide a spongy block 50, seen in FIG. 5, adhered by adhesive along the back or rear surface 25 of panel 20. The spongy block 50 is preferably a flat rectangular thin sponge provided with holes, such as hole 51, aligned respectively with the holes 34. The sponge tends to wipe the suture 40 as it is withdrawn therethrough. This provides a clean suture, free from kinks, knots and twists.

The sutures 40 are individually loaded into appropriate holes 34 and slots 36, according to the expected demand.

Since the needles 41 and the forward end portions of the sutures 40 are in juxtaposition along the front of the case, as shown in FIG. 1, they are easily observed, easily counted and readily withdrawn, as needed.

It will be obvious to those skilled in the art that many variations may be made in the embodiments here chosen for the purpose of illustranting without departing from the scope thereof as defined by the appended claims.

I claim:

1. A suture holding case comprising a panel provided with a plurality of holes therethrough for receiving therethrough and removably securing therein the intermediate portions of sutures with the end portions of such sutures hanging on opposite sides of said panel, fastening means above said holes for securing said panel to an instrument table and a bag suspended from said panel for receiving and confining the inner end portions of said sutures.

2. The suture holding case defined in claim 1 wherein said fastening means includes an adhesive strip along the inner surface of said panel above said holes.

3. The suture holding case defined in claim 1 wherein said holes are rectangular holes, said panel being provided with a slit adjacent to each of said holes which communicates with said hole for holding the sutures.

4. The suture holder defined in claim 1 wherein said bag is a flexible bag containing a pair of opposed walls which define a pocket provided with an upper opening below said panel and one of said walls is joined to the lower edge portion of one of said walls.

5. The suture holding case defined in claim 1 wherein said holes are arranged in spaced, transverse rows.

6. The suture holding case defined in claim 1 wherein said panel is a relatively rigid plastic sheet and wherein said bag is a flexible bag attached to said sheet.

7. The suture holding case defined in claim 1 including a sponge block secured to the surface of said panel and through which said sutures pass in passing through said holes.

8. The suture holding case defined in claim 1 wherein said holes constitute crossed slits.

9. The suture holding case defined in claim 1 wherein said panel is a rectangular panel and is composed of a sheet of relatively rigid material and wherein said bag is formed of a flexible web, said bag being secured by its edge portion to said panel and is disposed therebelow, said bag having an opening on one side of said panel for receiving said sutures.

10. The suture holding case defined in claim 1 wherein said holes are disposed in transverse parallel rows, the holes in one row being staggered with respect to the holes of an adjacent row.

11. The suture holding case defined in claim 1 wherein said fastening means includes an adhesive strip disposed adjacent to the upper edge portion on said panel, said adhesive strip having a removable cover strip thereover.

12. The suture holding case defined in claim 1 wherein indicia are located on the front of said panel adjacent to each of said holes for identifying the type and size of sutures carried by each hole.

13. The process of supplying sutures to a surgeon during a surgical operation comprising the steps of filling a suture holding case including suture storage panel having holes therethrough with assorted sutures by passing a portion of said sutures through said holes, removably supporting said sutures by intermediate portions of such sutures, supporting said suture holding case with the assorted sutures adjacent to the operating field, and withdrawing said sutures from said suture holding case as required by the surgeon during the surgical operation.

14. The process of supplying sutures to a surgeon during a surgical operation as defined in claim 13 further comprising the step of passing a portion of said sutures through a spongy material prior to passing said portion of said sutures through said holes in the storage panel of said suture holding case.

15. The process of supplying sutures to a surgeon during a surgical operation as defined in claim 13 further comprising the step of associating sutures of said holes in the storage panel of said given types and sizes together in suture holding case.

* * * * *